Figures 1, 2:
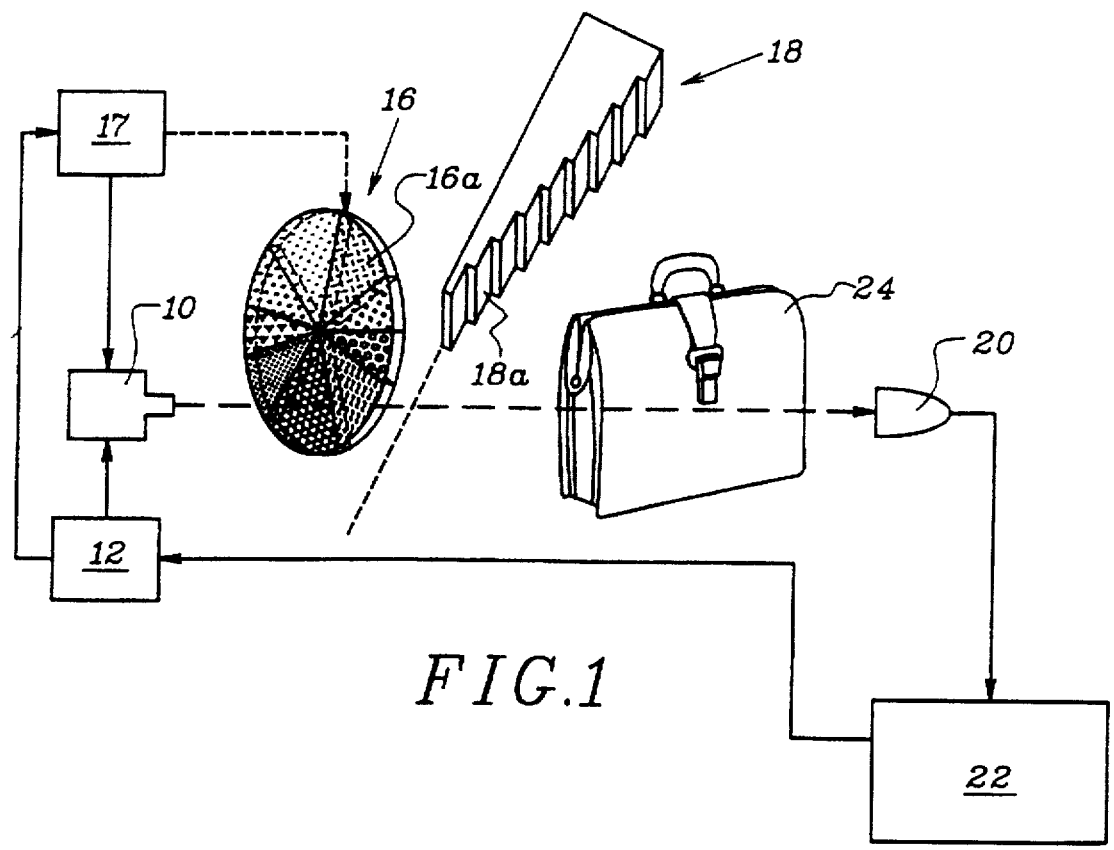

United States Patent [19]

Maitrejean et al.

[11] Patent Number: 5,687,210
[45] Date of Patent: Nov. 11, 1997

[54] METHOD AND DEVICE FOR DETERMINING THE ATTENUATION FUNCTION OF AN OBJECT WITH RESPECT TO THE TRANSMISSION OF A REFERENCE MATERIAL THICKNESS

[75] Inventors: Serge Maitrejean; Didier Perion, both of Paris, France

[73] Assignee: Europ Scan, Rungis Cedex, France

[21] Appl. No.: 553,427

[22] PCT Filed: May 16, 1994

[86] PCT No.: PCT/FR94/00581

§ 371 Date: Sep. 5, 1996

§ 102(e) Date: Sep. 5, 1996

[87] PCT Pub. No.: WO94/28398

PCT Pub. Date: Dec. 8, 1994

[30] Foreign Application Priority Data

May 28, 1993 [FR] France .................. 93 06449

[51] Int. Cl.[6] .................................. G01N 23/10
[52] U.S. Cl. .................................. 378/57; 378/56
[58] Field of Search .................... 378/53, 54, 55, 378/56, 57

[56] References Cited

U.S. PATENT DOCUMENTS

| | | |
|---|---|---|
| 4,400,827 | 8/1983 | Spears .................. 378/207 |
| 5,044,002 | 8/1991 | Stein .................... 378/54 |
| 5,479,023 | 12/1995 | Bartle ................. 250/390.04 |

FOREIGN PATENT DOCUMENTS

| | | |
|---|---|---|
| 394 654 | 5/1992 | Austria . |
| 0 334 762 | 9/1989 | European Pat. Off. . |
| 0 402 244 | 12/1990 | European Pat. Off. . |
| 2 004 437 | 3/1979 | United Kingdom . |
| WO 92/02892 | 2/1992 | WIPO . |

*Primary Examiner*—David P. Porta
*Assistant Examiner*—David Vernon Bruce
*Attorney, Agent, or Firm*—Lowe, Price, LeBlanc & Becker

[57] ABSTRACT

The object's transmission function is expressed as a finite power expansion of a reference-material reference thickness, each expansion power being equal to a ratio of a reference-material thickness to the reference thickness; the expansion coefficients are determined from the measurements of the intensities transmitted by the selected various thicknesses, including zero thickness, of the reference material exposed to a test beam evincing consecutively several energy spectra and from the measurements of the intensity transmitted by the object exposed to this same variable-spectrum test beam; the attenuation function is derived from the determination of the transmission function.

18 Claims, 2 Drawing Sheets

METHOD AND DEVICE FOR DETERMINING THE ATTENUATION FUNCTION OF AN OBJECT WITH RESPECT TO THE TRANSMISSION OF A REFERENCE MATERIAL THICKNESS

The present invention concerns a method for determining the attenuation function of an object and a device/apparatus with which to implement this method. In particular though not solely the invention relates to radioscopy. In general, it applies to the field of spectroscopy in the energy range from several Kev to several Mev.

As a rule the attenuation function of an object is not sought, instead only certain functional values at given energies. Thereupon the attenuation function can be reconstituted by interpolating a curve passing through said points. Foremost monochromatic x-ray or γ-ray beams of stable energy are used, which are obtained from isotope sources of which the energy might be lowered by the Compton effect, or from x-ray tubes with a broad spectrum filtered through a Bragg lattice to obtain a spectral-line spectrum.

The object to be measured must be placed in the beam path and a detector picks up the transmitted beam intensities for the various energies.

Letting $I_0(E)$ be the incident beam intensity, the energy being E, and letting $I_t$ be the transmitted beam intensity on the other side of the object, then the transmission Tr(E) for the energy E is the ratio $I_t(E)/I_0(E)$. The attenuation Att(E) at energy E is $-\log[Tr(E)]$.

These known techniques many incur many drawbacks. The particular attenuations are determined only for a slight number of energies. Consequently if the attenuation function must be ascertained, a curve must be made to fit said points, as a result of which accuracy depends on how the curve was interpolated.

Moreover the determination of the attenuation values by such techniques is time-consuming when an accuracy of about 1% is desired: a large number of measurements must be averaged and about one second is needed to ascertain an attenuation value.

The latter consideration precludes using these techniques for imaging, and even more so to make images in near real-time as is mandatory in luggage and security inspections.

One image comprises about 500 dots per line and about 600 lines; if each measurement requires one second, obtaining an image at a single energy requires about 83 h, which must be multiplied by the desired number of energies.

On the other hand Bragg diffraction and the Compton effect depend on the beam's angle of incidence and allow obtaining a beam of the desired energy only at a given angle of incidence when using a collimated beam. If using such a collimated beam, transmission measurement can take place only at one point in the object. To obtain simultaneously a large number of test points, the beam emission means must be multiplied because, considering the angular dependency, a fanning beam is precluded. It is clear that implementing such an assembly is highly complex and costly.

Isotope sources offer greater simplicity but also incur drawbacks: on account of safety precautions, the handling of such sources is rigorously prescribed, while beam intensity is low.

Accordingly the known procedures for measuring attenuation allow analysis only for specific energies strongly dependent on the equipment in use, but not on the user's wishes or needs. Moreover they are exceedingly time-consuming, costly and temperamental in operation; thus such techniques are hardly applicable in radioscopy or when used in security imaging, which represent important fields of application for object-attenuation determinations.

The present invention palliates these drawbacks. It allows determining the attenuation function very quickly (in tens of milliseconds) using x-ray tubes or standard γ-ray generators. The attenuation function is determined as a variable bijectively related to energy. As shown below, the transmission u of a reference thickness of a reference material is selected as the variable. When it is desired to state the attenuation by the object as an energy function, it will be sufficient to measure once (rather than at each determination) the transmission u for the desired energies, employing prior art techniques for that purpose.

More specifically, the invention concerns a method determining the attenuation function of an object and comprising the following stages:

A. stating the object's transmission function as a finite expansion in a power series of the transmission u of a reference-material reference thickness, each power u being assigned a coefficient, the expansion powers being equal to a ratio of previously determined reference-material thicknesses to the reference thickness, B. determining the expansion coefficients as follows:
  (a) measuring the intensity of a test beam for different energy spectra,
  (b) measuring, for each of said energy spectra, the beam intensity transmitted by each of the said reference-material thicknesses,
  (c) measuring, for each of said energy spectra, the beam intensity transmitted by the object,
  (d) for each of said spectra, resolving the object-transmitted beam intensity into a sum of the intensities measured in stage B-b relating to the considered spectrum, these intensities being assigned appropriate coefficients,
  (e) solving the system of equations set up in stage B-d, C. deriving from stages A and B the object's attenuation function expressed as a function of μ.

Said energy spectra are present within a range of 10 Kev to 500 Kev corresponding to the x-ray range or the energy spectra are present within a range of 0.5 Mev to 20 Mev corresponding to the γ-ray range. Advantageously said energy spectra are such that consecutive spectra will partly overlap.

To allow determination of the attenuation function, the number of reference-material reference thicknesses must be less than or equal to the number of energy spectra; illustratively N+1 energy spectra will be used, where N is an integer and $\geq 2$, and N reference-material reference thicknesses are exposed to these spectra. N may be 9 for instance.

Advantageously the expansion powers increased by ½ constitute a geometric progression with a ratio of a root of three, the first expansion power being zero.

In the sequence of the reference-material thicknesses, the order of the reference thicknesses determines the selection of a root of three. For instance if the reference thickness is selected as the third thickness in the reference-material sequence of thicknesses, the common ratio of the progression shall be the cube root of three. In this manner, zero and unity are part of the sequence. Zero corresponds to the power of u for free transmission, that is without a reference material in the path of the incident beam. Unity corresponds to the power of u for the transmission through the reference thickness. As regards the 10–500 Kev range, preferably the reference material shall be selected from the bodies with an effective atomic number Z between 5 and 26. In this manner the reference material shall have been selected with an average effective Z between the light and heavy materials.

For this 10–500 Kev range of energies, the reference material may be Duralumin. In that case the reference thickness will be between 1 and 5 mm. Advantageously the reference thickness is 4 mm.

When considering the 0.5–20 Mev energy range, the reference material is selected from the bodies with an effective atomic number Z between 13 and 60. Within said range, the reference material preferably shall be steel. The reference thickness in this range may be between 0.5 and 2 cm, advantageously it will be 1 cm.

To derive the attenuation function in terms of energy, that is, with energy the independent variable, the following additional stages are required:

measuring u as a function of energy using quasi-monochromatic energy beams of known intensities, deduce the values of the object's attenuation function for those energies.

The present invention also comprises apparatus with which to implement the above method and comprising:

means for emitting a test beam comprising a sequence of N+1 spectra of different energies, where N≧2 and an integer, N reference-material samples of different thicknesses, one of these thicknesses being selected as the reference thickness, and these samples lending themselves to be placed arbitrarily in the path of the beam, at least one detector able to measure beam intensity for each energy spectrum and also the beam intensities transmitted by the samples and the object exposed to the test beam, each detector is associated with appropriate data processing means able to calculate the object's transmission function from the beam-intensity measurements and from the intensity measurements of the beam transmitted by the samples and the object, and deriving the attenuation function expressed in relation to the transmission of the reference-material reference thickness.

In a variation, the method-implementing apparatus comprises:

means emitting a wide-spectrum test beam,

N samples of a reference material of different thicknesses, one of which shall be used as the reference thickness, where N≧2 and an integer, at least one stack of detectors each of which responds to a portion of the energy spectrum, said stacking being ordered from the detector responding to the lowest energy spectrum to the detector responding to the highest energy spectrum, each stack comprises data processing means at the outputs of the detectors of the particular stack to compute the object's transmission function from the intensity measurements of the various spectra of the test beam and from the intensity measurements of the spectra corresponding to the test beam transmitted by the samples and the object, and to derive therefrom the object's attenuation function expressed in terms of the transmission of the reference-material reference thickness.

The invention and its advantages are elucidated in the description below which is offered in illustrative and non-limiting manner and in relation to the attached drawings.

Figure 3:
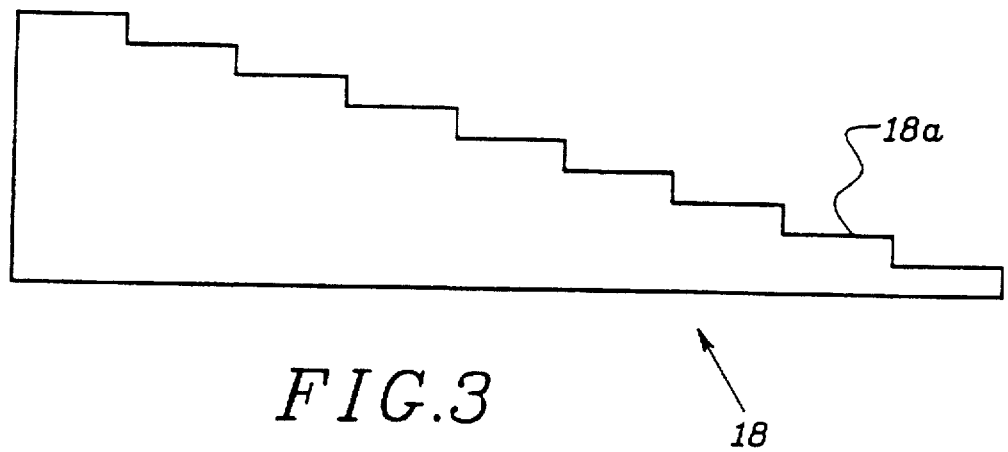
Figure 4:
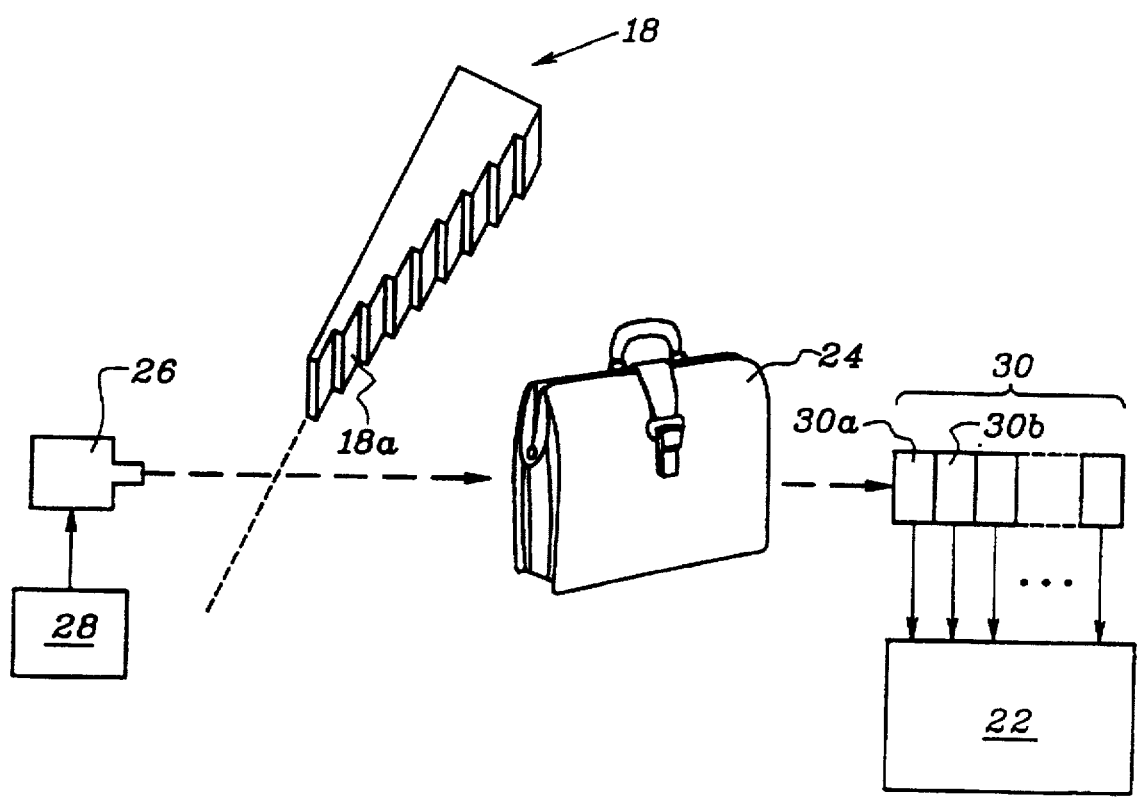

FIG. 1 schematically shown apparatus implementing the method of the invention,

FIG. 2 schematically shows a sequence of energy spectra used in measuring the transmissions, FIG. 3 schematically shows a longitudinal section of a stepped component, FIG. 4 schematically shows an embodiment variation of apparatus implementing the method of the invention.

A first apparatus implementing the method of the invention will now be described in relation to FIG. 1. This apparatus comprises an x-ray generator 10 with an energy range from 10 to 500 Kev or γ-rays with an energy range of 0.5 to 20 Mev, depending on the desired energy range. In this illustrative embodiment, the generator 10 controlled by a variable voltage source 12 emits a beam 14 with variable maximum energy.

A filter system 16 with various filters 16a sets in place the particular filter required for the given beam energy. In the illustration of FIG. 1, the filter system comprises a disk of which each portion corresponds to a different filter. These are high-pass filters and are known per se. Disk rotation is by a control 17 in turn connected to the control 12 to achieve synchronization.

Other filter systems may be used in equivalent manner, for instance consecutively arrayed filters may be translated into the beam path.

FIG. 2 shows the sequence of the consecutively resulting spectra when the disk is rotated in relation to beam energy. The filters are selected in such manner that the consecutive spectra will partly overlap.

Regarding the energy spectrum of the beam 14 from the generator 10, each filter suppresses all energies lower than an intrinsic threshold of the filter. Regarding each spectrum of FIG. 2, the high-energy portion corresponds to the maximum energy emitted by the generator 10 when the associated filter is placed in the beam path.

In practice the energy spectra are not sharply defined and their precise shape does not affect the measurement. On the other hand it is important that both the shape and the intensity of each spectrum remain constant during the time when the reference and the particular object are being measured.

The slight discontinuities in the sequence of spectra also leave the measurements unaffected. However, in order not to disturb the measurements, such discontinuities must be less than 5 Kev for the 20 to 40 Kev range and be less than 10 Kev for the higher ranges.

Referring to FIG. 1 again, it is seen that the apparatus comprises a stepped component 18. Each step corresponds to a sample of different thickness. FIG. 3 shows an illustrative component 18 in longitudinal section.

This component 18 is made of a reference material of which the effective Z may be between 5 and 26 for an incident beam of x-rays. Illustratively Duralumin is chosen (a mixture of 95% Al; 4.5% Cu and 0.5% Mn) of which the effective Z is approximately 13.5.

Regarding an incident beam of γ-rays, the reference material is selected from materials with an effective Z between 13 and 60. For instance steel, of which the effective Z is 26, will be selected.

The first step is selected as the step of least thickness, with the thickness increasing along the following steps.

In this embodiment, the thickness of the second step 18a is taken as the reference thickness. Obviously any other step also might be chosen as the reference step. For Duralumin, the reference thickness may be chosen within the range of 1 to 5 mm, for instance 4 mm.

The steel reference thickness may be chosen within the range from 0.5 to 2 cm, for instance 1 cm.

If the reference thickness is too slight, sensitivity at high energies will be degraded; if a the reference thickness is too large, low-energy sensitivity will suffer.

In general, a number N of distinct thicknesses of reference material and hence of steps in the component 18 is required when N+1 spectra are used. The component 18 shown in FIG. 3 comprises 9 steps and therefore is appropriate for apparatus using 10 energy spectra.

Again referring to FIG. 1, it is seen that the component 18 may be placed as desired, by translation, into the beam path. For clarity, the translating drive for the component 18 is omitted from FIG. 1.

The component 18 also may assume other shapes but equivalent ones to the one shown. For instance the component 18 may assume the shape of a disk of which the portions evince different thicknesses and of which one portion is clear to provide a free beam-path.

FIG. 1 shows that the apparatus includes a detector 20 delivering an electric signal proportional to fie beam intensity incident on it.

The detector 20 is connected to a control and processing system 22. This system 22 may be a computer for instance. The system 22 manages the variations of the variable-voltage control 12.

Presently the method of the invention determining an object's attenuation function will be described.

Calibration is carried out in a preliminary stage. Such calibration tests consist in measuring the intensity transmitted by the various reference-material reference thicknesses exposed to the test beam.

First this transmitted intensity is measured for zero thickness, that is with the component 18 outside the beam path.

Then the system 22 changes the variable voltage output and controls appropriate beam filtering by the filter system 16. Under the combined effect of voltage variation and appropriate filtration, the measuring beam 14 consecutively evinces N+1 different energy spectra. Illustratively N+1 may be 10.

Each beam-energy maximum is associated with a filter of the system 16 in order to consecutively obtain the different energy spectra. Each maximum-energy variation is synchronized with positioning a new filter.

Detector 20 measures the integrated intensity of the test beam for each of the spectra and these measurements are stored in the processing system 22.

Now the same measurements are repeated, but this time the different thicknesses of the reference material are consecutively placed into the beam path by translating the component 18. After these measurements have been stored in the system 22, the component is moved out of the beam path.

Accordingly, calibration is very quick. When the apparatus is used continuously, such calibration may be renewed several times daily: while the precise shape of each spectrum is not significant for measurement accuracy (the measurements being energy-integrated), on the other hand it is important that the shapes and intensities of the spectra be identical from one measurement to the next.

The object 24 to be analyzed is then placed in the beam path. This object 24 is consecutively exposed to each of the energy spectra obtained by varying the maximum energy of the beam in synchronization with appropriate filter insertion. The transmitted intensity of the object 24 is measured for each energy spectrum by the detector 20 and then is stored.

Thanks to these measurements, the system 22 deduces an analytical attenuation formula of the object where it was crossed by the beam, said attenuation being expressed in terms of a parameter u, that is, with u being the independent variable, which is the transmission of a given reference-material thickness.

The description below is restricted only the x-rays and to a Duralumin reference material. It is understood that the illustration is easily extended to the case of γ-rays and steel. The second step of the component 18 is selected as the reference thickness.

Accordingly $\mu = e^{-att(E)[2.7][0.4]}$ where 2.7 is the Duralumin density in g/cm$^3$ and 0.4 is the reference thickness selected to be 4 mm and expressed in cm.

In the invention, the system 22 implements the following method:

Letting the index j be the number of the spectrum applied to the object, then j=1 corresponds to the lowest energy spectrum, namely the most leftward of FIG. 2, whereas the intensity $D_j$ transmitted by the object is expressed as follows $$D_j = \int I_j(E) T_x(E) dE \qquad (0)$$

that is, $$D_j = \int I_j(E) e^{-att(E)} dE \qquad (1)$$

where $I_j$ is the intensity of the jth energy spectrum and is expresed in terms of the energy E, $T_x(E)$ and att(E) resp. are the transmission and attenuation functions here expressed in terms of E.

When changing variables, that is introducing the parameter u associated with the reference thickness ep (in cm) of the selected material of density p (in g/cm$^3$), one obtains $\mu = e^{-att(E)}(ep)(p)$ and $D_j$ becomes $$\mu = \int I'_j e^{-att'(u)} du \qquad (2)$$

where $I'_j$ is the intensity of the jth spectrum in terms of u and att'(u) is the desired attenuation function.

The object's transmission function is expressed in terms of the parameter u, that is, with u the independent variable. In a first stage, the system 22 implements this change of variable and then approximates as follows: the object's transmission function is expressed as a finite polynomial expansion in powers of the parameter u, that is $$e^{-att(u)} = \sum_{i=0}^{N} a_i u^{f(i)} \qquad (3)$$

where i is an index from 0 to N.

In practice this approximation was found highly accurate because the relative error so introduced is no mole than 10$^{-4}$.

The number of terms in the (N+1) expansion is less than or equal to the number of different energy spectra used for the transmission measurements and consequently it is equal to or less than N reference-material thicknesses used for calibration, plus 1.. Thereby each index i corresponds to a step number of the component 18, with the index 0 corresponding to zero thickness, in other words, the component is out of the beam path.

It is clear therefore that, at a given energy range, for instance the 10–150 Kev x-ray range, as the number of spectra increases, the interpolation shall improve. It can be shown that using a dozen spectra for an energy level of 140 Kev leads to an attenuation function at this level accurate to 10$^{-4}$.

For each value of i, the expansion power f(i) represents a ratio of one of the reference-material thicknesses to the reference thickness. Advantageously these ratios are such that the powers f(i) increased by ½ constitute a geometric progression with a common ratio that is a root of three.

This choice may be stated in mathematical form as follows:

$$f(i)+\tfrac{1}{2}=\alpha^i[f(0)+\tfrac{1}{2}]$$

Moreover f(0) is selected to be 0 because i=0 corresponds to the free beam path and hence to zero thickness:

$$f(i)=(\alpha^i-1)/2$$

In this manner if the second step is selected to be the reference thickness, f(2)=1 and consequently $\alpha=\sqrt{3}$.

When the second step 18a is chosen as the reference thickness, the ratio of the sequence equals the square root of three.

It may be shown that for this choice of the powers of the expansion and hence for the step thicknesses a well-behaved expansion may be achieved.

In fact and on account of the inevitable production tolerances, the terms f(i) do not precisely assume the calculated values. However such slight deviations do not affect the results' validity.

It can be shown that the object's transmitted intensity for the spectrum j can be resolved as $$D_j = \sum_{i=0}^{N} a_i C_{ji} \qquad (4)$$

wherein the terms $C_{ji}$ for each spectrum j correspond to the intensity transmitted by the various reference-material thicknesses, and i=0 corresponds to zero thickness, namely the component 18 being out of the beam path.

In eq. (4), the terms $D_j$ and $C_{ji}$ are known from measurement, only the coefficients $a_i$ being unknown. Including zero thickness, the number of reference-material thicknesses may be selected to be less than or equal to the number of spectra and thereupon the coefficients $a_i$ may be determined. In the presently discussed embodiment, six different energy spectra are used, the component 18 comprises nine steps, and the additional tests run when the component 18 was out of the beam path must also be included.

Consequently, during a subsequent stage and using the stored calibration values and the object's transmission measurements, the system 22 will determine the $a_i$ coefficients. Such calculation may be carried out by any known procedure, for instance that of the least squares.

The attenuation Att is defined as Att=−logTr, where Tr is the transmission.

After the coefficients $a_i$ have been determined, the system 22 replaces them by their values in eq. 3 and, taking their natural logs, multiplies them by (−1). In this manner the system 22 derives the attenuation function of the object 24 in terms of the parameter u.

FIG. 4 schematically shows an embodiment variation of the apparatus implementing the method of the invention.

In this variation, rather than consecutively testing the different energy spectra of the test beam, use is made of a test beam with a wide and fixed spectrum. The transmitted-intensity measurements from the component 18 or the object 24 are carried out by a stack 30 of detectors 30a, 30b ... each acting as a high-pass filter for the subsequent detectors. In this manner each detector emits an electric signal corresponding to the intensity for a specified portion of the wide energy spectrum.

It is clear that in the apparatus of FIG. 1, the objects being analyzed are exposed to a measuring beam consecutively evincing different energy spectra so as to sweep through the desired energy range, whereas in the apparatus of FIG. 4, the objects are exposed to a measuring beam with a wide spectrum corresponding to the desired energy, this wide spectrum subsequently being filtered by the various detectors.

The apparatus of FIG. 4 comprises a measuring-beam generator 26 which may be a generator of x- or γ-rays. This generator 26 is connected to a fixed-voltage control 28 whereby the measuring beam evinces a wide energy spectrum. The expression "wide-energy spectrum" denotes any energy range to be tested, for instance that of 10 to 500 Kev for x-rays or 0.5 to 20 Mev for γ-rays.

Similar to the previous embodiment, the apparatus of FIG. 4 comprises a reference-material stepped component of which the step thicknesses are specified. The component 18 may be displaced arbitrarily in the beam path or it may be positioned outside it thanks to an omitted translational motion.

Each detector 30a, 30b ... of the stack 30 is connected to the control and processing system 22. In this embodiment variation, the transmitted intensity measurements relating to each spectrum defined by filtering within the wide spectrum by means of the detectors are carried out simultaneously. The processing by the system 22 to derive the attenuation function is similar to that described above.

It may be desirable in some applications to derive the attenuation function not in terms of the parameter u but in terms of the energy. For that purpose it will be enough to measure once and for all, in a stage carried out beforehand, the transmission function of the reference-material reference thickness in terms of the energy. Such a measurement may be carried out by any known procedure: when this measurement has been taken once and for all, the constraints relating to time of set-up are acceptable enough to obtain the largest possible number of measurement points at the highest possible accuracy.

By measuring transmission for a large number of different energies, for instance 10 different energies within a range from 10 to 500 Kev, the transmission function of the reference-material reference thickness may be interpolated with an accuracy of $10^{-4}$.

When an object's attenuation function is desired to be measured in terms of energy, it is necessary therefore to store the transmission function u expressed in terms of energy in the memory of the system 22. Once the attenuation function has been determined in terms of the parameter u, it will suffice to replace u by its energy-equivalent to obtain the desired attenuation function.

The above description relates to measuring an object's attenuation function at a point in this object. To ascertain the attenuation function at every object point, one may use for instance a fan beam and a set of detectors, that is, as many detectors as desired points, which are arrayed along a line perpendicular to the median propagation direction of the beam. This apparatus allows deriving attenuation functions along a line, and the translation of the object allows measuring along consecutive lines.

We claim:

1. A method to determine an object's attenuation function, characterized in that it comprises the following stages:

A. expressing the object's transmission function as a finite power expansion of the transmission u of a reference-material reference thickness, each power of u being assigned a coefficient, the expansion powers being equal to a ratio between previously determined thicknesses of the reference material to the reference thickness, B. determining the expansion coefficients:
   (a) by measuring the intensity of a test beam for different energy spectra,
   (b) by measuring, for each of said energy spectra, the intensity of the beam transmitted by each of considered reference-material reference thicknesses,
   (c) by measuring, for each of said energy spectra, the object's transmitted beam intensity,
   (d) by resolving, for each of said energy spectra, the object's transmitted beam intensity into a sum of the intensities measured in the stage B-b relative to the spectrum under consideration, these intensities being assigned the looked-for coefficients,
   (e) by resolving the system of equations derived in the stage B-d, C. deriving the object's attenuation function in terms of u from the stages 1 and B.

2. Method defined in claim 1, characterized in that said energy spectra are present within a range of 10 Kev to 500 Kev.

3. Method defined in claim 1, characterized in that said energy spectra are present within a range of 500 Kev to 20 Mev.

4. Method defined in claim 1, characterized in that said energy spectra are partly overlapping with their neighbors.

5. Method defined in claim 1, characterized in that N+1 spectra are used, where N is an integer and $\geq 2$, and in that N reference-material thicknesses are exposed to these spectra.

6. Method defined in claim 5, characterized in that N=9.

7. Method defined in claim 1, characterized in that the expansion powers increased by ½ form a geometric progression with a common ratio equal to a root of three, the first power of the expansion being zero.

8. Method defined in claim 2, characterized in that the reference material is selected from bodies evincing an effective Z between 5 and 26.

9. Method defined in claim 8, characterized in that the reference material is Duralumin.

10. Method defined in claim 8, characterized in that the reference thickness is between 1 and 5 mm.

11. Method defined in claim 10, characterized in that the reference thickness is approximately 4 mm.

12. Method defined in claim 3, characterized in that the reference material is selected from the bodies evincing an effective Z between 13 and 60.

13. Method defined in claim 12, characterized in that the reference material is steel.

14. Method defined in claim 12, characterized in that the reference thickness is between 0.5 and 2 cm.

15. Method defined in claim 14, characterized in that the reference thickness is approximately 1 cm.

16. Method defined in claim 1, characterized in that it comprises the following additional stages:

measuring u in terms of energy using quasi-monochromatic energy beams of known intensities, deriving therefrom the values of the object's attenuation function for those energies.

17. Apparatus with which to implement the method of claim 1, characterized in that it comprises:

means (10, 16) emitting a test beam (14) sequentially evincing N+1 different energy spectra, where N is an integer and $\geq 2$, N samples of a reference material evincing different thicknesses, one of these thicknesses (18a) being selected as the reference thickness, said samples lending themselves to be placed arbitrarily in the path of the beam (14), at least one detector (20) to measure the intensity of the beam (14) for each energy spectrum and for measuring the intensities of the beams transmitted by the samples and by the object (24) exposed to the test beams, processing means (22) for each detector (20) that are able to calculate the object's transmission function from the measurement of beam intensity for each energy spectrum and from the measurement of the beam intensity transmitted by the samples and the object, and to derive therefrom the attenuation function expressed in terms of the reference-thickness transmission of the reference material.

18. Apparatus implementing the method defined in claim 1, characterized in that it comprises:

means (26) emitting a wide-spectrum test beam,

N samples made of a reference material and of different thicknesses, where $N \geq 2$ and an integer, one (18a) of said thicknesses being selected as the reference thickness, at least one detector stack (30), each detector 30a, 30b . . . ) responding to a portion of the energy spectrum, the stack being ordered from the detector responding to the weakest portion of the energy spectrum to the detector responding to the highest portion of the energy spectrum, processing means (22) for each stack (30) and connected at the outputs of the stacks under consideration, said processing means being able to calculate the object's transmission function from the measurement of the intensities of the different test-beam spectra, from the measurement of the intensities of the spectra corresponding to the test beam transmitted by the samples and the object, and to derive therefrom the object's attenuation function expressed in terms of the transmission of the reference-material reference thickness.

* * * * *